United States Patent [19]
Creasy et al.

[11] Patent Number: 6,159,716
[45] Date of Patent: Dec. 12, 2000

[54] HUMAN PROTEIN KINASE HOACF72

[75] Inventors: Caretha L. Creasy, Norristown; George P. Livi, Havertown; Damien J. Dunnington, King of Prussia; Usman Shabon, Swarthmore, all of Pa.

[73] Assignee: SmithKline Beecham Corporation, Philadelphia, Pa.

[21] Appl. No.: 09/350,484

[22] Filed: Jul. 9, 1999

Related U.S. Application Data

[62] Division of application No. 08/802,466, Feb. 19, 1997.
[51] Int. Cl.$^7$ .............................. C12N 9/00; C12N 21/06; A61K 39/395
[52] U.S. Cl. ....................... 435/183; 435/69.1; 424/130.1
[58] Field of Search .......................... 536/23.1; 435/183; 424/130.1

[56] References Cited

PUBLICATIONS

Tugendreich et al. "Linking yeast genetics to mammalian genomes: Identification and mapping of the human homolog of CDC27 via the expressed sequence tag (EST) data base", Proceedings of the National Academy of Sciences, vol. 90, pp. 10031–10035 (1993).
GenBank Accession No. Y09216.
GenBank Accession No. Y13493.
Copy of Partial European Search Report.
Pelech et al. "Protein kinase cascades in meiotic and mitotic cell cycle control", Biochem. Cell Biol., vol. 68, pp. 1297–1330 (1990).
Robey et al. "The cellular biology and molecular biochemistry of bone formation", Disorders of Bone and Mineral Metabolism, pp. 241–263 (1992).
Sanghera et al. "Identification of the Sites in Myelin Basic Protein That are Phosphorylated by Meiosis–Activated Protein Kinse p44$^{mpk}$", FEBS Letters, vol. 273, pp. 223–226 (1990).
Shah et al. "Engineering unnatural nucleotide specificity for rous sarcoma virus tyrosine kinase to uniquely label its direct substrates", P.N.A.S., vol. 94, pp. 3565–3570 (1997).
Song et al. "Isolation of Human and Murine Homologues of the Drosophila Minibrain Gene: Human Monologue Maps to 21 q22.2 in Down Syndrome Critical Region", Genomics, vol. 38, pp. 331–339 (1996).
Ward et al. "Suppression of a yeast cyclic–AMP–dependent protein kinase defect by overexpression of SOK1, a yeast gene exhibiting sequence similarity to a developmentally regulated mouse gene", Mol. Cell. Biol., vol. 14, pp. 5619–5627 (1994).
Woychik, "Regulating the Regulators", TIBS, vol. 19, pp. 103–105 (1994).
Garrett et al. "The *Saccharomyces cerevisiae* YAK1 Gene Encodes a Protein Kinase That is Induced by Arrest Early in the Cell Cycle", Mol. Cell. Biol., vol. 11(8), pp. 4045–4052 (1991).
Garrett et al. Loss of Ras activity in *Saccharomyces cerevisiae* is suppressed by distruptions of a new kinase gene, YAK1, whose product may act downstream of the camp–dependent protein kinase, Genes and Development, vol. 3, pp. 1336–1348 (1989).
Hartley et al. "The YAK1 protein kinase of *Saccharomyces cerevisiae* moderates thermotolerance and inhibits growth by an SCH9 protein kinase–independent mechanisms", Genetic, vol. 136, pp. 464–474, (1994).
House et al. "The Influence of Basic Residues on the Substrate Specificity of Protein Kinase C*", J. Biol. Chem., vol. 262, pp. 772–776.
Hunter et al. "The protein kinases of budding yeast: six score and more", Trends–Biochem–Sci, vol. 22, pp. 18–22 (1997).
Kentrup et al. "A duel specificity protein kinase with unique structural features whose activity is dependent on tyrosine residues between subdomains VII and VIII", J. Biol. Chem., vol. 271, pp. 3485–3488 (1996).
Lewis et al. "Definition of a Consensur Sequence for Peptide Substrate Recognition by p44$^{mpk}$ the Meiosis–activated Meylin Basic Protein Kinase", J. Biol. Chem., vol. 266, pp. 15180–15184 (1991).
Mundy "Is Prolonged stimulation of bone growth a therapeutic possibility?", Mol. Cell. Endocrinol., vol. 75, pp. C19–C25 (1991).
Hillier et al. "WashU–Merck EST Project", Accession No. T49193, (Feb. 8, 1995).
Venter et al., Trends in Biotechnology, vol. 10, pp. 8–11 (1992).
Charnock–Jones et al. Journal of Biotechnology, vol. 35, pp. 205–215 (1994).
Desnuelle et al. "Biochemical characterization of plasma membrane isolated from human skeletal muscle", FEBS Letters, vol. 188(2), pp. 222–226 (1985).

*Primary Examiner*—Ponnathapu Achutamurthy
*Assistant Examiner*—Christian L Fronda
*Attorney, Agent, or Firm*—William T. Han; Ratner & Prestia; William T. King

[57] ABSTRACT hYAK1 polypeptides and polynucleotides and methods for producing such polypeptides by recombinant techniques are disclosed. Also disclosed are methods for utilizing hYAK1 polypeptides and polynucleotides in the design of protocols for the treatment of bone loss including osteoporosis; inflammatory diseases such as Adult Respiratory Disease Syndrome (ARDS), Rheumatoid arthris, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others, and diagnostic assays for such conditions.

6 Claims, 2 Drawing Sheets

```
   1  GGAAACCTTCGGCCGCCGCTCCCGCCGCCTACCCGACCGATTGGCGGCAGTAAGCACACA    60
  61  ATGAATGATCACCTGCATGTCGGCAGCCACGCTCACGGACAGATCCAGGTTCAACAGTTG   120
      M  N  D  H  L  H  V  G  S  H  A  H  G  Q  I  Q  V  Q  Q  L
 121  TTTGAGGATAACAGTAACAAGCGGACAGTGCTCACGACACAACCAAATGGCTTACAACA    180
      F  E  D  N  S  N  K  R  T  V  L  T  T  Q  P  N  G  L  T  T
 181  GTGGGCAAAACGGGCTTGCCAGTGGTGCCAGAGCGGCAGCTGGACAGCATTCATAGACGG   240
      V  G  K  T  G  L  P  V  V  P  E  R  Q  L  D  S  I  H  R  R
 241  CAGGGGAGCTCCACCTCTCTAAAGTCCATGGAAGGCATGGGGAAGGTGAAAGCCACCCCC   300
      Q  G  S  S  T  S  L  K  S  M  E  G  M  G  K  V  K  A  T  P
 301  ATGACACCTGAACAAGCAATGAAGCAATACATGCAAAAACTCACAGCCTTCGAACACCAT   360
      M  T  P  E  Q  A  M  K  Q  Y  M  Q  K  L  T  A  F  E  H  H
 361  GAGATTTTCAGCTACCCTGAAATATATTTCTTGGGTCTAAATGCTAAGAAGCGCCAGGGC   420
      E  I  F  S  Y  P  E  I  Y  F  L  G  L  N  A  K  K  R  Q  G
 421  ATGACAGGTGGGCCCAACAATGGTGGCTATGATGATGACCAGGGATCATATGTGCAGGTG   480
      M  T  G  G  P  N  N  G  G  Y  D  D  D  Q  G  S  Y  V  Q  V
 481  CCCCACGATCACGTGGCTTACAGGTATGAGGTCCTCAAGGTCATTGGGAAGGGGAGCTTT   540
      P  H  D  H  V  A  Y  R  Y  E  V  L  K  V  I  G  K  G  S  F
 541  GGGCAGGTGGTCAAGGCCTACGATCACAAAGTCCACCAGCACGTGGCCCTAAAGATGGTG   600
      G  Q  V  V  K  A  Y  D  H  K  V  H  Q  H  V  A  L  K  M  V
 601  CGGAATGAGAAGCGCTTCCACCGGCAAGCAGCGGAGGAGATCCGAATCCTGGAACACCTG   660
      R  N  E  K  R  F  H  R  Q  A  A  E  E  I  R  I  L  E  H  L
 661  CGGAAGCAGGACAAGGATAACACAATGAATGTCATCCATATGCTGGAGAATTTCACCTTC   720
      R  K  Q  D  K  D  N  T  M  N  V  I  H  M  L  E  N  F  T  F
 721  CGCAACCACATCTGCATGACGTTTGAGCTGCTGAGCATGAACCTCTATAAGCTCATCAAG   780
      R  N  H  I  C  M  T  F  E  L  L  S  M  N  L  Y  K  L  I  K
 781  AAGAATAAATTCCAGGGCTTCAGTCTGCCTTTGGTTCGCAAGTTTGCCCACTCGATTCTG   840
      K  N  K  F  Q  G  F  S  L  P  L  V  R  K  F  A  H  S  I  L
 841  CAGTGCTTGGATGCTTTGCACAAAAACAGAATAATTCACTGTGACCTTAAGCCCGAGAAC   900
      Q  C  L  D  A  L  H  K  N  R  I  I  H  C  D  L  K  P  E  N
 901  ATTTTGTTAAAGCAGCAGGGTAGAAGCGGTATTAAAGTAATTGATTTTGGCTCCAGTTGT   960
      I  L  L  K  Q  Q  G  R  S  G  I  K  V  I  D  F  G  S  S  C
 961  TACGAGCATCAGCGTGTCTACACGTACATCCAGTCGCGTTTTTACCGGGCTCCAGAAGTG  1020
      Y  E  H  Q  R  V  Y  T  Y  I  Q  S  R  F  Y  R  A  P  E  V
1021  ATCCTTGGGGCCAGGTATGGCATGCCCATTGATATGTGGAGCCTGGGCTGCATTTTAGCA  1080
      I  L  G  A  R  Y  G  M  P  I  D  M  W  S  L  G  C  I  L  A
1081  GAGCTCCTGACGGGTTACCCCCTCTTGCCTGGGGAAGATGAAGGGGACCAGCTGGCCTGT  1140
      E  L  L  T  G  Y  P  L  L  P  G  E  D  E  G  D  Q  L  A  C
1141  ATGATTGAACTGTTGGGCATGCCCTCACAGAAACTGCTGGATGCATCCAAACGAGCCAAA  1200
      M  I  E  L  L  G  M  P  S  Q  K  L  L  D  A  S  K  R  A  K
1201  AATTTTGTGAGCTCCAAGGGTTATCCCCGTTACTGCACTGTCACGACTCTCTCAGATGGC  1260
      N  F  V  S  S  K  G  Y  P  R  Y  C  T  V  T  T  L  S  D  G
```

FIG. 1A

1261 TCTGTGGTCCTAAACGGAGGCCGTTCCCGGAGGGGGAAACTGAGGGGCCCACCGGAGAGC 1320
     S   V   V   L   N   G   G   R   S   R   R   G   K   L   R   G   P   P   E   S
1321 AGAGAGTGGGGTAACGCGCTGAAGGGGTGTGATGATCCCCTTTTCCTTGACTTCTTAAAA 1380
     R   E   W   G   N   A   L   K   G   C   D   D   P   L   F   L   D   F   L   K
1381 CAGTGTTTAGAGTGGGATCCTGCAGTGCGCATGACCCCAGGCCAGGCTTTGCGGCACCCC 1440
     Q   C   L   E   W   D   P   A   V   R   M   T   P   G   Q   A   L   R   H   P
1441 TGGCTGAGGAGGCGGTTGCCAAAGCCTCCCACCGGGGAGAAAACGTCAGTGAAAAGGATA 1500
     W   L   R   R   R   L   P   K   P   P   T   G   E   K   T   S   V   K   R   I
1501 ACTGAGAGCACCGGTGCTATCACATCTATATCCAAGTTACCTCCACCTTCTAGCTCAGCT 1560
     T   E   S   T   G   A   I   T   S   I   S   K   L   P   P   P   S   S   S   A
1561 TCCAAACTGAGGACTAATTTGGCGCAGATGACAGATGCCAATGGGAATATTCAGCAGAGG 1620
     S   K   L   R   T   N   L   A   Q   M   T   D   A   N   G   N   I   Q   Q   R
1621 ACAGTGTTGCCAAAACTTGTTAGCTGAGCTCACGTCCCCTGATGCTGGTAACCTGAAAGA 1680
     T   V   L   P   K   L   V   S   *
1681 TACGACATTGCTGAGCCTTACTGGGTTGAAAAGGAGTAGCTCAGACCTGTTTTTATTTGC 1740
1741 TCAATAACTCTACTCATTTGTATCTTTTCAGCACTTAATTTTAATGTAAGAAAGTTGTTC 1800
1801 ATTTTGTTTTTATAAAATACATGAGGACAATGCTTTAAGTTTTTATACTTTCAGAAACTT 1860
1861 TTTGTGTTCTAAAAGTACAATGAGCCTTACTGTATTTAGTGTGGCAGAATAATAACATCA 1920
1921 ATGGCAGGCCACTGATTACTTCATGACTGCCACGCATTTACAGATTGGTGTCAAAGACAT 1980
1981 TCACTATGTTTTTATGGTTCATGTTATATCCTCCCCAGGGTGACAGCCCCTTAAGGCCCT 2040
2041 CCTTTTCCCTCCATGCTCCAGGTCCATGCACAGGTGTAGCATGTC              2085

FIG. 1B

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 2085 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
GGAAACCTTC GGCCGCCGCT CCCGCCGCCT ACCCGACCGA TTGGCGGCAG TAAGCACAC      60

ATGAATGATC ACCTGCATGT CGGCAGCCAC GCTCACGGAC AGATCCAGGT TCAACAGT      120

TTTGAGGATA ACAGTAACAA GCGGACAGTG CTCACGACAC AACCAAATGG GCTTACAA      180

GTGGGCAAAA CGGGCTTGCC AGTGGTGCCA GAGCGGCAGC TGGACAGCAT TCATAGAC      240

CAGGGGAGCT CCACCTCTCT AAAGTCCATG GAAGGCATGG GGAAGGTGAA AGCCACCC      300

ATGACACCTG AACAAGCAAT GAAGCAATAC ATGCAAAAAC TCACAGCCTT CGAACACC      360

GAGATTTTCA GCTACCCTGA AATATATTTC TTGGGTCTAA ATGCTAAGAA GCGCCAGG      420

ATGACAGGTG GGCCCAACAA TGGTGGCTAT GATGATGACC AGGGATCATA TGTGCAGG      480

CCCCACGATC ACGTGGCTTA CAGGTATGAG GTCCTCAAGG TCATTGGGAA GGGGAGCT      540

GGGCAGGTGG TCAAGGCCTA CGATCACAAA GTCCACCAGC ACGTGGCCCT AAAGATGG      600

CGGAATGAGA AGCGCTTCCA CCGGCAAGCA GCGGAGGAGA TCCGAATCCT GGAACACC      660

CGGAAGCAGG ACAAGGATAA CACAATGAAT GTCATCCATA TGCTGGAGAA TTTCACCT      720

CGCAACCACA TCTGCATGAC GTTTGAGCTG CTGAGCATGA ACCTCTATAA GCTCATCA      780

AAGAATAAAT TCCAGGGCTT CAGTCTGCCT TTGGTTCGCA AGTTTGCCCA CTCGATTC      840

CAGTGCTTGG ATGCTTTGCA CAAAAACAGA ATAATTCACT GTGACCTTAA GCCCGAGA      900

ATTTTGTTAA AGCAGCAGGG TAGAAGCGGT ATTAAAGTAA TTGATTTTGG CTCCAGTT      960

TACGAGCATC AGCGTGTCTA CACGTACATC CAGTCGCGTT TTTACCGGGC TCCAGAA     1020

ATCCTTGGGG CCAGGTATGG CATGCCCATT GATATGTGGA GCCTGGGCTG CATTTTA     1080

GAGCTCCTGA CGGGTTACCC CCTCTTGCCT GGGGAAGATG AAGGGGACCA GCTGGCC     1140

ATGATTGAAC TGTTGGGCAT GCCCTCACAG AAACTGCTGG ATGCATCCAA ACGAGCC     1200

AATTTTGTGA GCTCCAAGGG TTATCCCCGT TACTGCACTG TCACGACTCT CTCAGAT     1260

TCTGTGGTCC TAAACGGAGG CCGTTCCCGG AGGGGGAAAC TGAGGGGCCC ACCGGAG     1320
```

```
AGAGAGTGGG GTAACGCGCT GAAGGGGTGT GATGATCCCC TTTTCCTTGA CTTCTTA      1380

CAGTGTTTAG AGTGGGATCC TGCAGTGCGC ATGACCCCAG GCCAGGCTTT GCGGCAC      1440

TGGCTGAGGA GGCGGTTGCC AAAGCCTCCC ACCGGGGAGA AAACGTCAGT GAAAAGG      1500

ACTGAGAGCA CCGGTGCTAT CACATCTATA TCCAAGTTAC CTCCACCTTC TAGCTCA      1560

TCCAAACTGA GGACTAATTT GGCGCAGATG ACAGATGCCA ATGGGAATAT TCAGCAG      1620

ACAGTGTTGC CAAAACTTGT TAGCTGAGCT CACGTCCCCT GATGCTGGTA ACCTGAA      1680

TACGACATTG CTGAGCCTTA CTGGGTTGAA AAGGAGTAGC TCAGACCTGT TTTTATT      1740

TCAATAACTC TACTCATTTG TATCTTTTCA GCACTTAATT TTAATGTAAG AAAGTTG      1800

ATTTTGTTTT TATAAAATAC ATGAGGACAA TGCTTTAAGT TTTTATACTT TCAGAAA      1860

TTTGTGTTCT AAAAGTACAA TGAGCCTTAC TGTATTTAGT GTGGCAGAAT AATAACA      1920

ATGGCAGGCC ACTGATTACT TCATGACTGC CACGCATTTA CAGATTGGTG TCAAAGA      1980

TCACTATGTT TTTATGGTTC ATGTTATATC CTCCCCAGGG TGACAGCCCC TTAAGGC      2040

CCTTTTCCCT CCATGCTCCA GGTCCATGCA CAGGTGTAGC ATGTC                   2085

(2) INFORMATION FOR SEQ ID NO: 2:

(i) SEQUENCE CHARACTERISTICS:
        (A) LENGTH: 528 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Met Asn Asp His Leu His Val Gly Ser His Ala His Gly Gln Ile Gln
 1               5                  10                  15

Val Gln Gln Leu Phe Glu Asp Asn Ser Asn Lys Arg Thr Val Leu Thr
            20                  25                  30

Thr Gln Pro Asn Gly Leu Thr Thr Val Gly Lys Thr Gly Leu Pro Val
        35                  40                  45

Val Pro Glu Arg Gln Leu Asp Ser Ile His Arg Gln Gly Ser Ser
    50                  55                  60

Thr Ser Leu Lys Ser Met Glu Gly Met Gly Lys Val Lys Ala Thr Pro
65                  70                  75                  80

Met Thr Pro Glu Gln Ala Met Lys Gln Tyr Met Gln Lys Leu Thr Ala
                85                  90                  95

Phe Glu His His Glu Ile Phe Ser Tyr Pro Glu Ile Tyr Phe Leu Gly
            100                 105                 110

Leu Asn Ala Lys Lys Arg Gln Gly Met Thr Gly Gly Pro Asn Asn Gly
        115                 120                 125

Gly Tyr Asp Asp Gln Gly Ser Tyr Val Gln Val Pro His Asp His
    130                 135                 140

Val Ala Tyr Arg Tyr Glu Val Leu Lys Val Ile Gly Lys Gly Ser Phe
145                 150                 155                 160

Gly Gln Val Val Lys Ala Tyr Asp His Lys Val His Gln His Val Ala
                165                 170                 175

Leu Lys Met Val Arg Asn Glu Lys Arg Phe His Arg Gln Ala Ala Glu
            180                 185                 190

Glu Ile Arg Ile Leu Glu His Leu Arg Lys Gln Asp Lys Asp Asn Thr
        195                 200                 205

Met Asn Val Ile His Met Leu Glu Asn Phe Thr Phe Arg Asn His Ile
```

-continued

```
            210                 215                 220
Cys Met Thr Phe Glu Leu Leu Ser Met Asn Leu Tyr Lys Leu Ile Lys
225                 230                 235                 240

Lys Asn Lys Phe Gln Gly Phe Ser Leu Pro Leu Val Arg Lys Phe Ala
                245                 250                 255

His Ser Ile Leu Gln Cys Leu Asp Ala Leu His Lys Asn Arg Ile Ile
                260                 265                 270

His Cys Asp Leu Lys Pro Glu Asn Ile Leu Leu Lys Gln Gln Gly Arg
            275                 280                 285

Ser Gly Ile Lys Val Ile Asp Phe Gly Ser Ser Cys Tyr Glu His Gln
        290                 295                 300

Arg Val Tyr Thr Tyr Ile Gln Ser Arg Phe Tyr Arg Ala Pro Glu Val
305                 310                 315                 320

Ile Leu Gly Ala Arg Tyr Gly Met Pro Ile Asp Met Trp Ser Leu Gly
                325                 330                 335

Cys Ile Leu Ala Glu Leu Leu Thr Gly Tyr Pro Leu Leu Pro Gly Glu
                340                 345                 350

Asp Glu Gly Asp Gln Leu Ala Cys Met Ile Glu Leu Leu Gly Met Pro
            355                 360                 365

Ser Gln Lys Leu Leu Asp Ala Ser Lys Arg Ala Lys Asn Phe Val Ser
    370                 375                 380

Ser Lys Gly Tyr Pro Arg Tyr Cys Thr Val Thr Thr Leu Ser Asp Gly
385                 390                 395                 400

Ser Val Val Leu Asn Gly Gly Arg Ser Arg Arg Gly Lys Leu Arg Gly
                405                 410                 415

Pro Pro Glu Ser Arg Glu Trp Gly Asn Ala Leu Lys Gly Cys Asp Asp
            420                 425                 430

Pro Leu Phe Leu Asp Phe Leu Lys Gln Cys Leu Glu Trp Asp Pro Ala
            435                 440                 445

Val Arg Met Thr Pro Gly Gln Ala Leu Arg His Pro Trp Leu Arg Arg
    450                 455                 460

Arg Leu Pro Lys Pro Pro Thr Gly Glu Lys Thr Ser Val Lys Arg Ile
465                 470                 475                 480

Thr Glu Ser Thr Gly Ala Ile Thr Ser Ile Ser Lys Leu Pro Pro Pro
                485                 490                 495

Ser Ser Ser Ala Ser Lys Leu Arg Thr Asn Leu Ala Gln Met Thr Asp
            500                 505                 510

Ala Asn Gly Asn Ile Gln Gln Arg Thr Val Leu Pro Lys Leu Val Ser
        515                 520                 525
```

HUMAN PROTEIN KINASE HOACF72

This application is a division of U.S. application Ser. No. 08/802,466, filed Feb. 19, 1997, whose contents are incorporated herein in their entirety

FIELD OF THE INVENTION

This invention relates to newly identified polynucleotides, polypeptides encoded by them and to the use of such polynucleotides and polypeptides, and to their production. More particularly, the polynucleotides and polypeptides of the present invention relate to a protein serine/threonine kinase, hereinafter referred to as hYAK1. The invention also relates to inhibiting or activating the action of such polynucleotides and polypeptides.

BACKGROUND OF THE INVENTION

A number of polypeptide growth factors and hormones mediate their cellular effects through a signal transduction pathway. Transduction of signals from the cell surface receptors for these ligands to intracellular effectors frequently involves phosphorylation or dephosphorylation of specific protein substrates by regulatory protein serine/threonine kinases (PSTK) and phosphatases. Serine/threonine phosphorylation is a major mediator of signal transduction in multicellular organisms. Receptor-bound, membrane-bound and intracellular PSTKs regulate cell proliferation, cell differentiation and signalling processes in many cell types.

Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are potential targets for drug design.

A subset of PSTKs are involved in regulation of cell cycling. These are the cyclin-dependent kinases or CDKs (Peter and Herskowitz, Cell 1994: 79, 181–184). CDKs are activated by binding to regulatory proteins called cyclins and control passage of the cell through specific cell cycle checkpoints. For example, CDK2 complexed with cyclin E allows cells to progress through the GI to S phase transition. The complexes of CDKs and cyclins are subject to inhibition by low molecular weight proteins such as p16 (Serrano et al, Nature 1993: 366, 704), which binds to and inhibits CDK4. Deletions or mutations in p16 have been implicated in a variety of tumors (Kamb et al, Science 1994: 264, 436–440). Therefore, the proliferative state of cells and diseases associated with this state are dependent on the activity of CDKs and their associated regulatory molecules. In diseases such as cancer where inhibition of proliferation is desired, compounds that inhibit CDKs may be useful therapeutic agents. Conversely, activators of CDKs may be useful where enhancement of proliferation is needed, such as in the treatment of immunodeficiency.

YAK1, a PSTK with sequence homology to CDKs, was originally identified in yeast as a mediator of cell cycle arrest caused by inactivation of the cAMP-dependent protein kinase PKA (Garrett et al, Mol Cell Biol. 1991: 11, 4045–4052). YAK1 kinase activity is low in cycling yeast but increases dramatically when the cells are arrested prior to the S-G2 transition. Increased expression of YAK1 causes growth arrest in yeast cells deficient in PKA. Therefore, YAK1 can act as a cell cycle suppressor in yeast.

Frequently, in disease such as osteoporosis and osteoarthritis, patients have established lesions of bone or cartilage, respectively. Treatment of such lesions requires an agent that will stimulate new bone or cartilage formation to replace that lost to the disease; therefore, there is a need for drugs that increase the number of osteoblasts or chondrocytes, the cells responsible for bone or cartilage formation, respectively. Similarly, replacement of heart or skeletal muscle depleted by diseases such as myocardial infarction or HIV-associated cachexia requires drugs that stimulate proliferation of cardiac myocytes or skeletal myoblasts. The present invention describes a novel human homolog of yeast YAK1 termed hYAK1, which is expressed in osteoblasts, chondrocytes, cardiac and skeletal muscle, and at lower levels, in placenta and pancreas. The sequence of hYAK1 shares homology with predicted PSTKs from C. elegans, S. pombe and S. cerevisiae and has motifs associated with known protein kinases. Inhibitors of hYAK1 are expected to stimulate proliferation of cells in which it is expressed.

This indicates that these protein serine/threonine kinases have an established, proven history as therapeutic targets. Clearly there is a need for identification and characterization of further members of the protein serine threonine kinase family which can play a role in preventing, ameliorating or correcting dysfunctions or diseases, including, but not limited to, bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to hYAK1 polypeptides and recombinant materials and methods for their production. Another aspect of the invention relates to methods for using such hYAK1 polypeptides and polynucleotides. Such uses include the treatment of bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with hYAK1 imbalance with the identified compounds. Yet another aspect of the invention relates to diagnostic assays for detecting diseases associated with inappropriate hYAK1 activity or levels.

BRIEF DESCRIPTION OF THE DRAWINGS

FIGS. 1A and 1B show the nucleotide and deduced amino acid sequence from a human hYAK1. SEQ ID NOS: 1 and 2.

DESCRIPTION OF THE INVENTION

Definitions

The following definitions are provided to facilitate understanding of certain terms used frequently herein.

"hYAK1" refers, among others, generally to a polypeptide having the amino acid sequence set forth in SEQ ID NO:2 or an allelic variant thereof.

"hYAK1 activity or hYAK1 polypeptide activity" or "biological activity of the hYAK1 or hYAK1 polypeptide" refers to the metabolic or physiologic function of said hYAK1 including similar activities or improved activities or these activities with decreased undesirable side-effects. Also included are antigenic and immunogenic activities of said hYAK1.

"hYAK1 gene" refers to a polynucleotide having the nucleotide sequence set forth in SEQ ID NO: 1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzmol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A.M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S.F. et al., *J Molec Biol* (1990) 215:403).

Polypeptides of the Invention

In one aspect, the present invention relates to hYAK1 polypeptides. The hYAK1 polypeptides include the polypeptide of SEQ ID NO:2; as well as polypeptides comprising the amino acid sequence of SEQ D NO: 2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Also included within hYAK1 polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Preferably hYAK1 polypeptide exhibit at least one biological activity of hYAK1.

The hYAK1 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the hYAK1 polypeptides are also included in the invention. A fragment is a polypeptide having an amino acid sequence that entirely is the same as part, but not all, of the amino acid sequence of the aforementioned hYAK1 polypeptides. As with hYAK1 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of hYAK1 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of hYAK1 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate hYAK1 activity, including those with a similar activity or an improved activity, or with a decreased undesirable activity. Also included are those that are antigenic or immunogenic in an animal, especially in a human.

Preferably, all of these polypeptide fragments retain the biological activity of the hYAK1, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The hYAK1 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art Polynucleotides of the Invention Another aspect of the invention relates to hYAK1 polynucleotides. hYAK1 polynucleotides include isolated polynucleotides which encode the hYAK1 polypeptides and fragments, and polynucleotides closely related thereto. More specifically, hYAK1 polynucleotide of the invention include a polynucleotide comprising the nucleotide sequence set forth in SEQ ID NO:1 encoding a hYAK1 polypeptide of SEQ ID NO: 2, and polynucleotide having the particular sequence of SEQ ID NO: 1. hYAK1 polynucleotides further include a polynucleotide comprising a nucleotide sequence that has at least 80% identity to a nucleotide sequence encoding the hYAK1 polypeptide of SEQ ID NO:2 over its entire length, and a polynucleotide that is at least 80% identical to that having SEQ ID NO: 1 over its entire length. In this regard, polynucleotides at least 90% identical are particularly preferred, and those with at least 95% are especially preferred Furthermore, those with at least 97% are highly preferred and those with at least 98–99% are most highly preferred, with at least 99% being the most preferred. Also included under hYAK1 polynucleotides are a nucleotide sequence which has sufficient identity to a nucleotide sequence contained in SEQ ID NO: 1 to hybridize under conditions useable for amplification or for use as a probe or marker. The invention also provides polynucleotides which are complementary to such hYAK1 polynucleotides. hYAK1 of the invention is structurally related to other proteins of the protein serine/threonine kinase family, as shown by the results of sequencing the cDNA encoding human hYAK1. The cDNA sequence contains an open reading frame encoding a polypeptide of 528 amino acids. Amino acid of sequence of FIGS. 1A and 1B (SEQ ID NO:2) has about 65% identity (using FASTA) in 456 amino acid residues with C. elegans protein kinase F49E11.1 (Wilson et al., Nature 368:32–38, 1994). Furthermore, hYAK1 is 46% identical to S. pombe protein kinase SPAC2F7.03c over 336 amino acids (Barrell et al., Schizosaccahromyces pombe chromosome I sequencing project, 1995) and 46% identical to S. cerevisiae protein kinase YAK1 over 267 amino acids (Garrett and Broach, Genes & Develop. 3:1336–1348, 1989). Nucleotide sequence of FIGS. 1A and 1B (SEQ ID NO:1) has about 67% identity (using FASTA) in 1129 nucleotide residues with C. elegans protein kinase F49E1 1.1 (Wilson et al., Nature 368:32–38, 1994).

One polynucleotide of the present invention encoding hYAK1 may be obtained using standard cloning and screening, from a cDNA library derived from mR in cells of human osteosarcoma, chondrosarcoma, osteoblast, heart and leukocyte using the expressed sequence tag (EST) analysis (Adams, M. D., et al. *Science* (1991) 252:1651–1656; Adams, M. D. et al., *Nature,* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding hYAK1 polypeptide of SEQ ID NO:2 may be identical over its entire length to the coding sequence set forth in FIG. 1 (SEQ ID NO: 1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention comprise a nucleotide sequence that is highly identical, at least 80% identical, with a nucleotide sequence encoding a hYAK1 polypeptide, or at least 80% identical with the sequence contained in FIGS. 1A and 1B (SEQ ID NO: 1) encoding hYAK1 polypeptide, or at least 80% identical to a nucleotide sequence encoding the polypeptide of SEQ ID NO:2.

When the polynucleotides of the invention are used for the recombinant production of hYAK1 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize MRNA.

Further preferred embodiments are polynucleotides encoding hYAK1 variants comprise the amino acid sequence hYAK1 polypeptide of FIGS. 1A and 1B (SEQ ID NO:2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein abovedescribed polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO:1, may be used as hybridization probes for cDNA and genomic DNA, to isolate full-length cDNAs and genomic clones encoding hYAK1 polypeptide and to isolate cDNA and genomic clones of other genes that have a high sequence similarity to the hYAK1 gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding hYAK1 comprises the steps of screening an appropriate library under stingent hybridization conditions with a labeled probe having the SEQ ID NO: 1 or a fragment thereof; and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15mM trisodium citrate), 50 mM sodium phosphate (pH7.6), 5× Denhardt's solution, 10 % dextran sulfate, and 20 microgram/ml denatured, sheared salmon sperm DNA, followed by washing the filters in 0.1× SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*,

*Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the hYAK1 polypeptide is to be expressed for use in screening assays, generally, it is preferred that the polypeptide be produced at the surface of the cell. In this event, the cells may be harvested prior to use in the screening assay. If hYAK1 polypeptide is secreted into the medium, the medium can be recovered in order to recover and purify the polypeptide; if produced intracellularly, the cells must first be lysed before the polypeptide is recovered. hYAK1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of hYAK1 polynucleotides for use as diagnostic reagents. Detection of a mutated form of hYAK1 gene associated with a dysfunction will provide a diagnostic tool that can add to or define a diagnosis of a disease or susceptibility to a disease which results from under-expression, over-expression or altered expression of hYAK1. Individuals carrying mutations in the hYAK1 gene may be detected at the DNA level by a variety of techniques.

Nucleic acids for diagnosis may be obtained from a subjects cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled hYAK1 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method See Cotton et al., *Proc Natl Acad Sci USA* (1985) 85: 4397–4401. In another embodiment, an array of oligonucleotides probes comprising hYAK1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et al., Science, Vol 274, pp 610–613 (1996)).

The diagnostic assays offer a process for diagnosing or determining a susceptibility to bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, deliriun, dementia, severe mental retardation and dysinesias, such as Huntington's disease or Gilles dela Tourett's syndrome through detection of mutation in the hYAK1 gene by the methods described.

In addition, bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of hYAK1 polypeptide or hYAK1 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an hYAK1 polypeptide, in a sample derived from a host are well-known to those of skill in the art. Such assay methods include radioimunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the hYAK1 polypeptides. The term "immunospecific" means that the antibodies have substantiall greater affinity for the polypeptides of the invention than their affinity for other related polypeptides in the prior art.

Antibodies generated against the hYAK1 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp.77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against hYAK1 polypeptides may also be employed to treat bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with hYAK1 polypeptide, or a fragment thereof, adequate to produce antibody and/or T cell immune response to protect said animal from bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises, delivering hYAK1 polypeptide via a vector directing expression of hYAK1 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a hYAK1 polypeptide wherein the composition comprises a hYAK1 polypeptide or hYAK1 gene. The vaccine formulation may further comprise a suitable carrier. Since hYAK1 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The hYAK1 polypeptide of the present invention may be employed in a screening process for compounds which activate (agonists) or inhibit activation of (antagonists, or otherwise called inhibitors) the hYAK1 polypeptide of the present invention. Thus, polypeptides of the invention may also be used to assess identify agonist or antagonists from, for example, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et al., *Current Protocols in Immunology* 1(2):Chapter 5 (1991).

hYAK1 polypeptides are ubiquitous in the mammalian host and are responsible for many biological functions, including many pathologies. Accordingly, it is desirous to find compounds and drugs which stimulate hYAK1 polypeptide on the one hand and which can inhibit the function of hYAK1 polypeptide on the other hand. In general, agonists are employed for therapeutic and prophylactic purposes for such conditions as bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as bone loss including osteoporosis; inflammatory diseases such as Adult Respiratory Disease Syndrome (ARDS), Rheumatoid arthritis, Osteoarthritis, inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Giles dela Tourett's syndrome.

In general, such screening procedures may involve using appropriate cells which express the hYAK1 polypeptide or respond to hYAK1 polypeptide of the present invention. Such cells include cells from mammals, yeast, Drosophila or *E. coli*. Cells which express the hYAK1 polypeptide (or cell membrane containing the expressed polypeptide) or respond to hYAK1 polypeptide are then contacted with a test compound to observe binding, or stimulation or inhibition of a functional response. The ability of the cells which were contacted with the candidate compounds is compared with the same cells which were not contacted for hYAK1 activity.

The knowledge that the hYAK1 encodes a protein kinase suggests that recombinant forms can be used to establish a protein kinase activity. Typically this would involve the direct incubation of hYAK1 with a protein or peptide substrate in the presence of $\gamma$-$^{32}$P-ATP, followed by the measurement of radioactivity incorporated into the substrate by separation and counting. Separation methods include immunoprecipitation, conjugation of substrate to a bead allowing separation by centrifugation or determination of incorporation by scintillation proximity assay, SDS-PAGE followed by autoradiography or biosensor analysis. While the specific substrates are not yet known, candidates include hYAK1 itself (autophosphorylation), myelin basic protein, casein, histone and HSP27. Other substances might be discovered by incubating hYAK1 with random peptides conjugated to solid supports or displayed on the surface of phage or by incubation of hYAK1 with mammalian cell lysates and $\gamma$-$^{32}$P-ATP, followed by separation of the labelled target proteins, and sequencing. The protein kinase activity of hYAK1 may require incubation with a specific upstream effector. This may be achieved by preincubating hYAK1 with lysates from a variety of stimulated eukaryotic cells and ATP. These assays permit the discovery and modification of compounds which inhibit hYAK1 kinase activity in vitro and would be expected to have effects on proliferation of osteoblasts, chondorcytes, cardiac myocytes or skeletal myoblasts. Any inhibitors so identified would be expected to have up-regulatory effects on proliferation and be useful as a therapeutic for the treatment and prevention of diseases such as osteoporosis, osteoarthritis, cardiomyopathy and chachexia.

This invention contemplates the treatment and/ or amelioration of such diseases by administering a hYAK1 inhibiting amount of a compound. Without wishing to be bound by any particular theory of the functioning of the hYAK1 of this invention, it is believed that among the useful inhibitors of hYAK1 function are those compounds which inhibit the kinase activity of the hYAK1. Other sites of inhibition are, of course, possible owing to its position in a signal transduction cascade. Therefore, inhibiting the interaction of hYAK1 with one or more of its upstream or downstream modulators/substrates is also contemplated by this invention. Inhibitors of protein-protein interactions between hYAK1 and other factors could lead to the development of pharmaceutical agents for the modulation of hYAK1 activity.

The assays may simply test binding of a candidate compound wherein adherence to the cells bearing the hYAK1 polypeptide is detected by means of a label directly or indirectly associated with the candidate compound or in an assay involving competition with a labeled competitor. Further, these assays may test whether the candidate compound results in a signal generated by activation of the hYAK1 polypeptide, using detection systems appropriate to the cells bearing the hYAK1 polypeptide. Inhibitors of activation are generally assayed in the presence of a known agonist and the effect on activation by the agonist by the presence of the candidate compound is observed. Standard methods for conducting such screening assays are well understood in the art.

Examples of potential hYAK1 polypeptide antagonists include antibodies or, in some cases, oligonucleotides or proteins which are closely related to the ligands, substrates, receptors, etc., as the case may be, of the hYAK1 polypeptide, e.g., a fragment of the ligands, substrates, receptors, or small molecules which bind to the polypeptide of the present invention but do not elicit a response, so that the activity of the polypeptide is prevented.

Prophylactic and Therapeutic Methods

This invention provides methods of treating an abnormal conditions related to both an excess of and insufficient amounts of hYAK1 polypeptide activity.

If the activity of hYAK1 polypeptide is in excess, several approaches are available. One approach comprises administering to a subject an inhibitor compound (antagonist) as hereinabove described along with a pharmaceutically acceptable carrier in an amount effective to inhibit activation by blocking binding of ligands to the hYAK1 polypeptide, or by inhibiting a second signal, and thereby alleviating the abnormal condition.

In another approach, soluble forms of hYAK1 polypeptides still capable of binding the ligand in competition with endogenous hYAK1 polypeptide may be administered. Typical embodiments of such competitors comprise fragments of the hYAK1 polypeptide.

In still another approach, expression of the gene encoding endogenous hYAK1 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression,* CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of hYAK1 and its activity, several approaches are also available. One approach comprises administering to a subject a therapeutically effective amount of a compound which activates hYAK1 polypeptide, i.e., an agonist as described above, in combination with a pharmaceutically acceptable carrier, to thereby alleviate the abnormal condition. Alternatively, gene therapy may be employed to effect the endogenous production of hYAK1 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996).

Formulation and Administration

Peptides, such as the soluble form of hYAK1 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the lie.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject

EXAMPLES

The examples below are carried out using standard techniques, which are well known and routine to those of skill in the art, except where otherwise described in detail. The examples illustrate, but do not limit the invention.

EXAMPLE 1

A partial clone (ATG-355, HGS EST #454640) was initially identified through random searches of the Human Genome Sciences database. This partial clone (~1 kb) showed significant homology to YAK1 from S cerevisiae. To get the full length cDNA: A total of 1M plaques were screened from a Human Osteoblast cDNA library (Stratagene, LaJolla Calif.) using the insert of the above partial clone as a probe. Library screening procedure is described by (Elgin, et al. Stratagies 4: 8–9, 1991). The probes were $\alpha$-32P labeled, using Random Primed Labeling Kit (Boheringer Manheim, Germany, Cat. # 1585584 ) and purified by running over Sephadex G-50 columns (Pharmacia Biotech. Cat. # 17-0855-02) The hybirdization and washing conditions were according to ( J. Sambrook, E. F. Fritch and T. Maniatis (1989) A Laboratory Manaul Second. Ed. Vol. 1 pp. 2.69–2.81 Cold Spring Harbor Laboratory Press, Cold Spring Harbor, N.Y.). Five clones were isolated by plaque purification and a fragments containing the inserts were excised and sequenced. The longest insert was a 2.7 kb fragment containing the 3' untranslated region and part of the coding sequence of hYAK1. A second probe prepared by EcoRI-BamHI digestion of this insert followed by labelling with 32P was used to screen a commercially available human heart cDNA library (Stratagene #936207). An additional five clones were plaque purified, excised into phagemids and sequenced. Fasta analysis show this peptide to have high homology to a putative serine/threonine kinase of unknown function from C. elegans (F49E1 1.1).

To confirm that the cDNA was full length, Huaaan Leukocyte "Marathon Ready" cDNA (Clontech, Palo Alto, Calif.) was used as a template to amplify a fragment corresponding to the 5' region of hYAK1 using a 5' anchor primer-1 (Clontech) and a reverse gene specific primer. This fragment was T/A cloned into pCR2.1 vitrogen), and multiple isolates were sequenced. An in-frame stop codon was identified upstream of the predicted initiation codon confirming that the full length cDNA had been obtained.

Northern analysis was carried out to determine the distribution of hYAK1 MRNA in human tissues. A fragment containing the 3' untranslated region of hYAK1 was isolated from SEQ ID NO:1 using standard techniques. The isolated fragment was radiolabelled with $\alpha$-$^{32}$P-dATP using a randomly primed labelling kit. Membranes containing mRNA from multiple human tissues (Clontech #7760-1) were hybridized with the probe and washed under high stringency conditions as directed Hybridized MRNA was visualized by exposing the membranes for 4 days to X-ray film. Three major transcripts of 2.6, 7 and 10 kb were present and were expressed most prominently in heart and skeletal muscle, but were present to a lesser degree in pancreas, placenta and brain. All three transcripts appeared absent from kidney

What is claimed is:

1. A hYAK1 polypeptide comprising an amino acid sequence which is at least 80% identical to the amino acid sequence of SEQ ID NO:2 over its entire length.

2. The polypeptide of claim 1 which comprises the amino acid sequence of SEQ ID NO:2.

3. The polypeptide of SEQ ID NO: 2.

4. A hYAK1 polypeptide prepared by culturing a host cell comprising an expression vector encoding an amino acid sequence having at least 80% identity over its entire length to the amino acid sequence of SEQ ID NO:2 and recovering the polypeptide from the culture.

5. An antibody immunospecific for the hYAK1 polypeptide of claim 1.

6. A polypeptide obtainable by expressing a nucleotide sequence comprising the sequence of SEQ ID NO: 1.

* * * * *